United States Patent
Zhang et al.

(10) Patent No.: US 10,774,386 B2
(45) Date of Patent: Sep. 15, 2020

(54) SERUM OR PLASMA MICRORNA AS BIOMARKERS FOR NON-SMALL CELL LUNG CANCER

(71) Applicant: Micromedmark Biotech Co., Ltd., Beijing (CN)

(72) Inventors: Chenyu Zhang, Beijing (CN); Ke Zeng, Beijing (CN); Junfeng Zhang, Beijing (CN); Yi Ba, Beijing (CN); Xi Chen, Beijing (CN); Haijin Li, Beijing (CN)

(73) Assignee: MICROMEDMARK BIOTECH CO., LTD., Beijing (CN)

( * ) Notice: Subject to any disclaimer, the term of this patent is extended or adjusted under 35 U.S.C. 154(b) by 472 days.

(21) Appl. No.: 15/206,797

(22) Filed: Jul. 11, 2016

(65) Prior Publication Data

US 2016/0312310 A1    Oct. 27, 2016

Related U.S. Application Data

(63) Continuation of application No. 12/996,967, filed as application No. PCT/CN2009/001441 on Dec. 14, 2009, now Pat. No. 9,388,470.

(30) Foreign Application Priority Data

Dec. 15, 2008  (CN) .......................... 2008 1 0243501

(51) Int. Cl.
 *C12Q 1/6886* (2018.01)
 *C12N 15/113* (2010.01)

(52) U.S. Cl.
 CPC ...... *C12Q 1/6886* (2013.01); *C12Q 2600/112* (2013.01); *C12Q 2600/118* (2013.01); *C12Q 2600/158* (2013.01); *C12Q 2600/16* (2013.01); *C12Q 2600/178* (2013.01)

(58) Field of Classification Search
 None
 See application file for complete search history.

(56) References Cited

U.S. PATENT DOCUMENTS

| | | | |
|---|---|---|---|
| 6,194,454 B1 | 2/2001 | Dow | |
| 7,709,616 B2 | 5/2010 | Bentwich et al. | |
| 2009/0131348 A1 | 5/2009 | Labourier et al. | |
| 2010/0178653 A1 | 7/2010 | Aharonov et al. | |
| 2010/0323357 A1 | 12/2010 | Nana-Sinkam et al. | |

FOREIGN PATENT DOCUMENTS

| | | |
|---|---|---|
| CN | 101307361 | 11/2008 |
| CN | 101384273 A | 3/2009 |
| CN | 101389770 A | 3/2009 |
| CN | 101475984 | 7/2009 |
| EP | 2 133 431 A1 | 12/2009 |
| WO | WO 2007/073737 A1 | 7/2007 |
| WO | WO 2007/081740 A2 | 7/2007 |
| WO | WO 2009/055979 A1 | 5/2009 |

OTHER PUBLICATIONS

Iorio et al (Cancer Res 2005; 65(16): 7065-7070, Aug. 15, 2005) (Year: 2005).*
Thompson et al (Nature Methods 1(1): 1-7, 2004) (Year: 2004).*
Thompson et al (Nature Methods 1(1): 1-7, 2004) Supplemental Figure 1 (Year: 2004).*
Lu et al (Nature 435:834-838, 2005) (Year: 2005).*
Lu et al (Nature 435:834-838, 2005), Supplementary Table 1 (Year: 2005).*
Lu et al (Nature 435:834-838, 2005), Supplementary Information (Year: 2005).*
Ahern (1995) (retrieved from http://www.the-scientist.library.upenn.edu/yr1995/july/tools_950724.html) (Year: 1995).*
Chen, et al. 2008 "Characterization of microRNAs in serum: a novel class of biomarkers for diagnosis of cancer and other diseases" *Cell Research* 18: 997-1006.
Baskerville, et al. 2005 "Microarray profiling of microRNAS reveals frequent coexpression with neighboring miRNAs and host genes" *RNA* 11: 241-247.
Lee, E.J. et al. 2006 "Expression profiling identifies microRNA signature in pancreatic cancer" *Int J Cancer* 120: 1046-1054.
Liu, J. et al. 2009 "Research advancement of microRNA on pancreatic cancer" *Progress in Modern Biomedicine* 9: 4560-4564.
Qin, Y. et al. 2007 "Research advances in the detection of microRNA" *Journal of Medical Postgraduates* 20: 1198-1201.
Wang, J. et al. 2009 "MicroRNAs in plasma of pancreatic ductal adenocarcinoma patients as novel blood-based biomarkers of disease" *Cancer Prev Res* 2: 807-813.

\* cited by examiner

*Primary Examiner* — Richard A Schnizer
(74) *Attorney, Agent, or Firm* — Knobbe, Martens, Olson & Bear, LLP

(57) ABSTRACT

Provided are non-small cell lung cancer markers and the use thereof in diagnosing and monitoring diseases in vitro. The non-small cell lung cancer markers include at least one of 26 selected detectable mature microRNAs existing stably in human serum or plasma. Also provided are probe combinations, a kit and a biochip for detecting the non-small cell lung cancer markers. The invention further provides a method for detecting the said lung cancer markers. The method in the present invention enables extensive detection spectrum, high sensitivity, low cost, convenient sample taking and preservation. The method can be applied in the general survey of disease, solves problems of low specificity and sensitivity encountered with previous single markers, and increases significantly the clinical detection rate of diseases. The methods provide an effective means for diagnosing diseases at an early stage.

13 Claims, 6 Drawing Sheets

Specification includes a Sequence Listing.

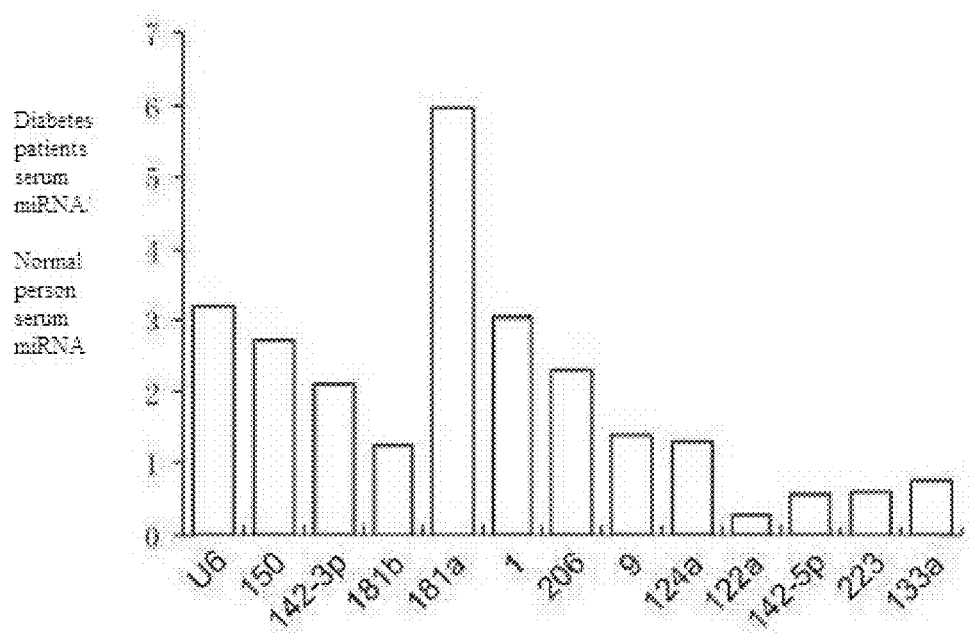
Fig.4-A
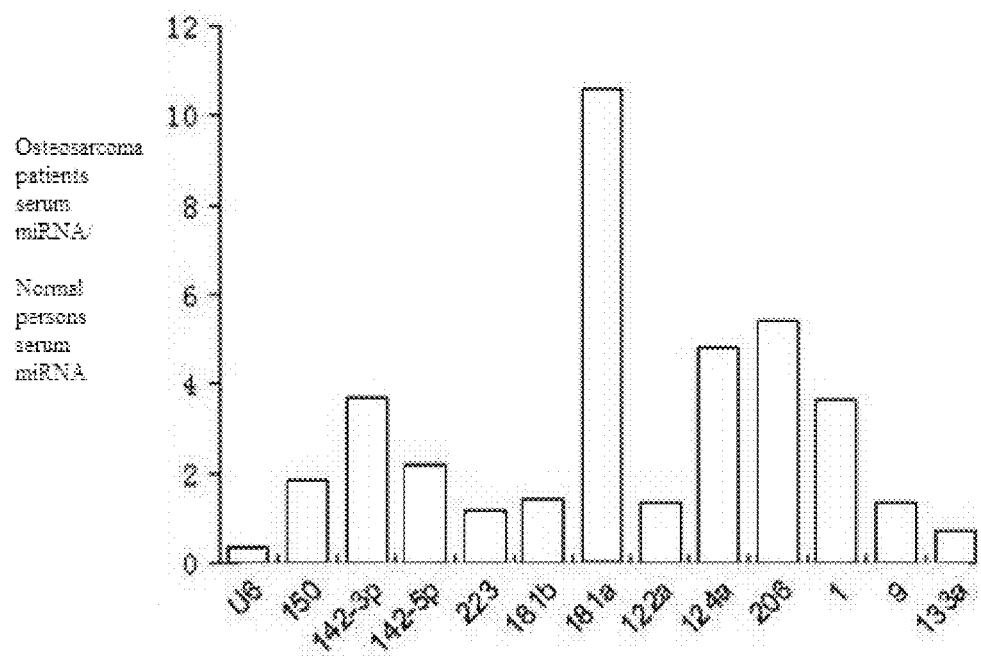
Fig. 4-B

SERUM OR PLASMA MICRORNA AS BIOMARKERS FOR NON-SMALL CELL LUNG CANCER

FIELD OF THE INVENTION

The present invention relates to serum or plasma microRNAs for non-small cell lung cancer.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 23732198_1. TXT, the date of creation of the ASCII text file is Jul. 11, 2016 and the size of the ASCII text file is 6.15 KB.

BACKGROUND OF THE INVENTION

The present invention relates to biological diagnostic techniques, and more specifically to the separation and the qualitative and quantitative analysis of microRNAs in human serum or plasma, and to clinical indicators of non-small cell lung cancer. More particularly, the invention relates to a method for detecting and analyzing variations in microRNAs in human serum or plasma. This enables in vitro diagnosis of non-small cell lung cancer; evaluation of disease stage; monitoring of the progression of non-small cell lung cancer; evaluation of disease complications and relapse; prognosis of non-small cell lung cancer; and evaluation of drug efficacy and therapeutic effects.

Non-small cell lung cancer is the most common type of lung cancer, which comprises of 85% of all lung cancer cases. The accurate location and precise detection of non-small cell lung cancer markers is an important precondition for early diagnosis and treatment of non-small cell lung cancer.

Although many disease markers have been discovered and applied in the general survey and diagnosis of clinical diseases and in the monitoring of therapeutic efficacy, obvious deficiencies exist in their clinical application. For instance, the tumor markers that have been widely used in clinical diagnosis, including alpha-fetoprotein (AFP), lactic dehydrogenase (LHD) and carcinoembryonic antigen (CEA), are inadequate for the early stage diagnosis of cancers for various reasons. For example, the sensitivity and specificity of the disease markers mentioned above are relatively low, so that the detection results cannot be used as accurate indicators for disease diagnosis. Furthermore, the disease markers mentioned above cannot satisfy the requirement for early stage diagnosis, which often bears a positive correlation with the therapeutic efficacy. Due to drawbacks including the extremely high specificity of cancer differentiation types, the relatively low sensitivity of tumor bodies, the difficulty of taking repetitive samples, the high requirements for preserving samples, and the expensive costs, the application of the currently known tumor markers cannot be widely promoted under present conditions. Meanwhile, some conventional medical methods such as biopsy for tissue and cell detection have inherent deficiencies, such as taking sample from an incorrect location, insufficiency of tissue and cell sample materials, or the technician's lack of experience, which may all contribute to misdiagnosis. Other techniques like medical imaging that have been widely used in disease inspection and diagnosis are rather limited in the qualitative description of disease process. Therefore, it is necessary to find new types of disease markers that are sensitive and convenient in application, and capable of overcoming the deficiencies of the currently known markers.

Micro ribonucleic acids (microRNAs or miRNAs) are a class of non-coding, single strand, small ribonucleic acid molecules having a length of 19 to 23 nucleotides. They are highly conserved in evolution and closely related to many normal biophysical activities of animals, including ontogenesis, tissue differentiation, apoptosis and energy metabolism, and to the occurrence and progression of many diseases. Recent research has found that the expression level of several microRNAs in chronic lymphocytic leukemia and Burkett lymphoma patients is down-regulated to varying extents (Lawrie C H, Gal S, Dunlop H M et al. Detection of elevated levels of tumor-associated microRNAs in serum of patients with diffuse large B-cell lymphoma. Br J Haematol 2008; 141:672-675); the analysis of the expression of microRNAs in human lung cancer and breast cancer tissues shows that the expression level of some tissue-specific microRNAs is different from that of normal tissues (Garofalo M, Quintavalle C, Di Leva G et al. MicroRNA signatures of TRAIL resistance in human non-small cell lung cancer. Oncogene 2008). There is also research proving that microRNAs influence the occurrence and progression of angiocardiopathies including cardiac hypertrophy, heart failure and atherosclerosis, and are closely related to metabolic diseases like diabetes type II (Tryndyak V P, Ross S A, Beland F A, Pogribny I P. Down-regulation of the microRNAs miR-34a, miR-127 and miR-200b in rat liver during hepatocarcinogenesis induced by a methyl-deficient diet. Mol Carcinog. 2008 Oct. 21). All of these studies conclude that the expression and specific variations of microRNAs are related to the occurrence and progression of diseases.

MicroRNAs play a highly important role in post-transcription gene regulation, which indicates a relationship between microRNAs and diseases. Firstly, the variations of microRNAs may be the cause of the diseases, because the disease inhibition and promotion factors are probably the targets of microRNAs. MicroRNA expression disorders, for example, down-regulation of genes expressing microRNAs that inhibit the disease promotion factors, or up-regulation of genes expressing microRNAs that inhibit the disease inhibition factors, would lead to down-stream gene expression variation and even lead to some gene-pathway disorders, eventually causing diseases. Secondly, microRNA variations are probably the result of the diseases. Disease (cancers, for instance) may cause loss of chromosome sections, genetic mutation or sudden amplification of chromosome sections; if the microRNAs are from the varied sections, the expression level of these microRNAs will be tremendously altered. Therefore, theoretically, microRNAs can be used as a novel disease marker; the specific alteration is undoubtedly related to disease occurrence and development. Meanwhile, microRNAs may be potential drug target sites; the occurrence and progression of the diseases may be largely relieved by inhibiting up-regulated microRNAs or over-expressing down-regulated microRNAs during the disease progression.

Presently, research on microRNAs as disease markers has been carried out in China. For instance, Chinese patent applications CN100999765A and CN101298630A have disclosed respectively that, in the case of colon cancer, specific variations have occurred to some microRNAs when benign colon polyps deteriorate into malignant tumor. A more sensitive and accurate early-phase colon cancer diagnosis method has been developed according to the specific variations of microRNAs. However, the wide clinical application is restrained by difficulties in obtaining tissue samples.

SUMMARY OF THE INVENTION

The present invention provides methods for detecting non-small cell lung cancer by determining the content of microRNAs in serum/plasma. The methods comprise detecting one or more of the microRNAs selected from the group consisting of miR-7, miR-20a, miR-23b, miR-24, miR-25, miR-27a, miR-29a, miR-30d, miR-99a, miR-125b, miR-144, miR-145, miR-146a, miR-152, miR-182, miR-199a-5p, miR-199a-3p, miR-221, miR-222, miR-223, miR-320, miR-375, miR-382, miR-423-5p, miR-432 and miR-584.

The invention also provides microRNA probes based on these microRNAs for use in the methods. The probes are used to make reagents, diagnostic kits and biochips for detecting non-small cell lung cancer.

BRIEF DESCRIPTION OF THE DRAWINGS

FIGS. 4A and 4B show the content variations of the partial microRNAs in the serum of diabetes and osteosarcoma patients, respectively compared to the normal subjects.

DETAILED DESCRIPTION OF THE INVENTION

Figure 1:
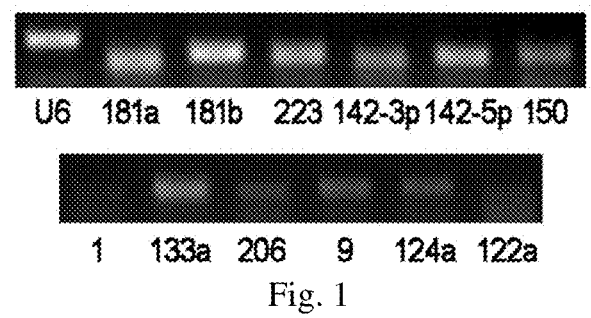
FIG. 1 shows the RT-PCR results of partial microRNAs directly detected in the serum of a normal subject.

In order to overcome the deficiencies defects of the currently applied diagnosis techniques described above, the present inventors have focused on blood that is relatively easy to obtain and even can be collected via routine physical examination. Blood circulates through the body and carries oxygen and nutrients to and waste materials away from all body tissues and cells. Therefore, blood could reflect the physiological and pathological condition of an organism, and the detecting results can function as indicators for human health. It is known that in serum/plasma there are various kinds of proteins such as total protein, albumin and globulin; lipids such as HDL cholesterol and triglycerides; carbohydrates; pigments; electrolytes; inorganic salts; and enzymes such as amylase, alkaline phosphatase, acid phosphatase, cholinesterase and aldolase; moreover, there also exist many kinds of signaling molecules from tissues and organs throughout the body such as cytokines and hormones. Currently, disease diagnosis is limited to the above-mentioned biochemical indicators in serum/plasma, and there is no report that serum/plasma microRNAs can be used as markers. It is traditionally believed that there are no microRNAs in serum/plasma, and that, if any, it will be rapidly degraded by RNase into small molecule segments and hence cannot be detected. However, microRNAs, consisting of 19 to 23 nucleotides, possess specificity and relative stability in structure and have been discovered to exist in serum/plasma. The preliminary research of the inventor has proven that microRNAs stably exist, and various diseases have a matching profile of microRNAs (Chen et al: Characterization of microRNAs in serum: a novel class of markers for diagnosis of cancer and other diseases. Cell Res. 2008 October; 18 (10):997). In order to locate and accurately detect the non-small cell lung cancer markers, according to the currently available research results, the inventor has performed research with respect to the following aspects:

(1) researching the specific variations of serum or plasma microRNAs during the pathogenesis of non-small cell lung cancer;

(2) detecting the variations of serum or plasma microRNAs of non-small cell lung cancer patients by using biochip and sequencing techniques for detecting serum or plasma microRNAs;

(3) applying screened serum or plasma microRNA molecules that exhibit significant differences between non-small cell lung cancer and normal physiological conditions to the research of detection technique of serum or plasma microRNAs, in order to prepare biochips and kits for the diagnosis of non-small cell lung cancer and the like.

Based on the researches on the relationship between the serum or plasma microRNAs and non-small cell lung cancer described above, the present invention provides microRNAs that exist stably in serum or plasma which can be used as detection markers of non-small cell lung cancer. The invention also provided a method to detect in vitro the microRNAs existing stably in serum or plasma, which enables the early stage diagnosis of non-small cell lung cancer, the identification of the disease, the monitoring on disease process, the prediction on the relapse, prognosis and complication occurrence of the disease, by detecting the specific variations of certain microRNAs. The invention further provides improved assessment of drug efficacy, medication guidance, treatment of individuals, screening for active ingredients of Chinese Traditional Medicines, and research on population taxonomy.

Therefore, the present invention provides markers existing stably in human serum or plasma that can be used for the diagnosis of non-small cell lung cancer.

The present invention also provides a probe combination for detecting the non-small cell lung cancer markers.

The present invention further provides a method for detecting the above-mentioned non-small cell lung cancer markers.

The present invention further provides the use of the above-mentioned non-small cell lung cancer markers in the preparation of kits and biochips.

The aims of the present invention are achieved by the technical solutions which follow.

In one aspect, the present invention provides non-small cell lung cancer markers, which comprise at least one, and may be any number between 1-26, the mature microRNAs that exist stably in human serum or plasma and are detectable, such as microRNAs: miR-7, miR-20a, miR-23b, miR-24, miR-25, miR-27a, miR-29a, miR-30d, miR-99a, miR-125b, miR-144, miR-145, miR-146a, miR-152, miR-182, miR-199a-5p, miR-199a-3p, miR-221, miR-222, miR-223, miR-320, miR-375, miR-382, miR-423-5p, miR-432 and miR-584.

The present invention also provides non-small cell lung cancer markers, which comprise two or more, and may be any number between 2-26, of the mature microRNAs that exist stably in human serum or plasma and are detectable, such as microRNAs: miR-7, miR-20a, miR-23b, miR-24, miR-25, miR-27a, miR-29a, miR-30d, miR-99a, miR-125b, miR-144, miR-145, miR-146a, miR-152, miR-182, miR-199a-5p, miR-199a-3p, miR-221, miR-222, miR-223, miR-320, miR-375, miR-382, miR-423-5p, miR-432 and miR-584.

The serum or plasma can be obtained from living bodies, tissues, organs and/or corpses of human beings.

In another aspect, the present invention provides a method to detect the markers, which comprises RT-PCR assay, Real-time PCR assay, Northern blotting assay, RNase protection assay, Solexa sequencing technique or the biochip method.

Preferably, the method comprises the RT-PCT assay, including the following steps:
1) extracting total RNA from the serum or plasma of the subject, and obtaining cDNA samples by the RNA reverse transcription reaction; or, collecting serum or plasma samples of the subjects and preparing cDNA samples by the reverse transcription reaction with the serum or plasma as a buffer solution;
2) carrying out PCR reaction with primers designed with the microRNAs;
3) performing Agarose Gel Electrophoresis of PCR products;
4) observing the products under ultra-violet light after EB staining.

Alternatively, the method comprises Real-time PCR assay, including the following steps:
1) extracting total RNA from the subject serum or plasma, and preparing cDNA products by the RNA reverse transcription reaction; or, collecting serum or plasma samples of the subjects, and preparing the cDNA samples by the reverse transcription reaction with the serum or plasma as a buffer solution;
2) designing primers with the microRNAs;
3) placing fluorescent label on the probes and performing the PCR reaction;
4) detecting variations in the content of microRNAs in the serum or plasma samples and making a comparison of them with those in normal serum or plasma.

Specifically, the method to detect the markers in the serum or plasma of a subject according to the present invention can be used to evaluate the condition of a non-small cell lung cancer patient. The method to detect the microRNAs that exist stably and are detectable in human serum or plasma involves the use of one or more of RT-PCR assay, Real-time PCR assay, Northern blotting assay, RNase protection assay, Solexa sequencing technique and the biochip method.

RT-PCR assay includes the following steps: (1) collecting serum or plasma samples through extracting total RNA from the serum or plasma with Trizol reagent, and then preparing cDNA samples by the RNA reverse transcription reaction; or, collecting serum or plasma samples of the subject, and preparing cDNA samples by the reverse transcription reaction with the serum or plasma as a buffer solution; (2) performing PCR reaction with primers designed with microRNAs; (3) performing Agarose Gel Electrophoresis with PCR products; (4) observing the products under ultra-violet light after EB staining.

Real-time PCR assay includes the following steps: (1) collecting the serum or plasma samples through extracting total RNA from the serum or plasma with the reagents such as Trizol reagent, and then obtaining cDNA samples by the RNA reverse transcription reaction; or, preparing cDNA samples by the reverse transcription reaction with the serum or plasma as a buffer solution; (2) designing primers with the microRNAs; (3) placing fluorescent probes, such as EVA GREEN, and performing PCR reaction; (4) analyzing the processing data and comparing the results, specifically, detecting the variations of microRNAs in the serum or plasma samples and comparing them with those in the normal serum or plasma.

Northern blotting assay includes the following steps: (1) collecting serum or plasma samples; (2) extracting total RNA from the serum or plasma samples with Trizol reagent; (3) performing denaturing PAGE electrophoresis and membrane transfer procedures; (4) preparing the isotope labeling microRNA probes; (5) performing the membrane hybridizing reaction; (6) detecting isotope signals, e.g. the results of P-screen scanning.

The RNase protection assay includes the following steps: (1) preparing probes for anti-sense RNAs, and performing the isotope labeling and purification; (2) collecting serum or plasma samples and extracting the RNAs; (3) dissolving the extracted RNAs into a hybridizing buffer solution, placing the anti-sense RNA probes and performing the hybridizing reaction; (4) adding the RNase digestion solution and performing the reaction; (5) performing the electrophoresis and autoradiography; (6) analyzing the results.

Solexa sequencing technique includes the following steps: (1) collecting serum or plasma samples; (2) extracting the total RNA from the serum or plasma samples with Trizol reagent; (3) performing PAGE electrophoresis and collecting the 17-27 nt RNA molecules; (4) connecting the adaptor prime enzymes to the 3' and 5' end of the RNA molecules; (5) sequencing after the RT-PCR reaction; (6) analyzing and processing the data.

The biochip method includes the following steps: (1) preparing a lattice of all the more than 500 mature microRNAs of human beings and the biochips thereof; (2) collecting serum or plasma samples; (3) extracting total RNA from the serum or plasma samples; (4) separating the microRNAs with separating columns; (5) performing the fluorescent labeling on the microRNAs with the T4 RNA connection enzyme; (6) performing the hybridizing reaction with the biochips; (7) examining and analyzing the data.

The present invention provides a method for determining the variations in the content of microRNAs in the serum or plasma of non-small cell lung cancer patients in all progressive stages. The relationship between the microRNAs and non-small cell lung cancer may be determined by using the techniques of RT-PCR assay, Real-time PCR assay, Northern blotting assay, the RNase protection assay, Solexa sequencing technique and the biochip method, and the like, in which the variations of miR-7, miR-20a, miR-23b, miR-24, miR-25, miR-27a, miR-29a, miR-30d, miR-99a, miR-125b, miR-144, miR-145, miR-146a, miR-152, miR-182, miR-199a-5p, miR-199a-3p, miR-221, miR-222, miR-223, miR-320, miR-375, miR-382, miR-423-5p, miR-432 and miR-584 from the non-small cell lung cancer patients are detected and analyzed. Biochips of the serum or plasma microRNAs are prepared, and the variations of the serum or plasma microRNAs of non-small cell lung cancer patients are detected, while Solexa sequencing analysis is performed on the microRNAs in the serum or plasma of the patients suffering from non-small cell lung cancer.

The serum or plasma used in the method can be obtained from living bodies, tissues, organs and/or corpses of the subjects.

The present invention also provides a method to predict, diagnose and/or evaluate non-small cell lung cancer, which includes detecting the markers mentioned above. Preferably, the method includes detecting the markers mentioned above using the aforesaid detecting techniques.

The present invention provides a use of the above-mentioned markers of non-small cell lung cancer in the preparation of reagents or tools for the prediction, diagnosis and/or evaluation of non-small cell lung cancer.

The present invention also provides a microRNA probe combination used for detecting the marker of non-small cell lung cancer, that is, a microRNA probe combination for detecting non-small cell lung cancer. The aforesaid probe combination comprises at least one, and may be any number between 1-26, of the probes that match the following RNA sequences. Preferably, the probe combination comprises two or more, and may be any number between 2-26, of the probes that match the following RNA sequences:

| microRNA | Matching probe sequence | SN. of the sequence |
|---|---|---|
| miR-7 | CAACAAAATCACTAGTCTTCCA | SEQ ID NO. 1 |
| miR-20a | CTACCTGCACTATAAGCACTTTA | SEQ ID NO. 2 |
| miR-23b | GGTAATCCCTGGCAATGTGAT | SEQ ID NO. 3 |
| miR-24 | CTGTTCCTGCTGAACTGAGCCA | SEQ ID NO. 4 |
| miR-25 | TCAGACCGAGACAAGTGCAATG | SEQ ID NO. 5 |
| miR-27a | GCGGAACTTAGCCACTGTGAA | SEQ ID NO. 6 |
| miR-29a | AACCGATTTCAGATGGTGCTA | SEQ ID NO. 7 |
| miR-30d | CTTCCAGTCGGGGATGTTTACA | SEQ ID NO. 8 |
| miR-99a | CACAAGATCGGATCTACGGGTT | SEQ ID NO. 9 |
| miR-125b | TCACAAGTTAGGGTCTCAGGGA | SEQ ID NO. 10 |
| miR-144 | CTAGTACATCATCTATACTGTA | SEQ ID NO. 11 |
| miR-145 | AAGGGATTCCTGGGAAAACTGGAC | SEQ ID NO. 12 |
| miR-146a | AACCCATGGAATTCAGTTCTCA | SEQ ID NO. 13 |
| miR-152 | CCCAAGTTCTGTCATGCACTGA | SEQ ID NO. 14 |
| miR-182 | TGTGAGTTCTACCATTGCCAAA | SEQ ID NO. 15 |
| miR-199a-5P | GAACAGGTAGTCTGAACACTGGG | SEQ ID NO. 16 |
| miR-199a-3P | TAACCAATGTGCTCTGATGACA | SEQ ID NO. 17 |
| miR-221 | GAAACCCAGCAGACAATGTAGCT | SEQ ID NO. 18 |
| miR-222 | GAGACCCAGTAGCCAGATGTAGCT | SEQ ID NO. 19 |
| miR-223 | GGGGTATTTGACAAACTGACA | SEQ ID NO. 20 |
| miR-320 | TTCGCCCTCTCAACCCAGCTTTT | SEQ ID NO. 21 |
| miR-375 | TCACGCGAGCCGAACGAACAAA | SEQ ID NO. 22 |
| miR-382 | CGAATCCACCACGAACAACTTC | SEQ ID NO. 23 |
| miR-423-5P | CTGAGGGGCCTCAGACCGAGCT | SEQ ID NO. 24 |
| miR-432 | CCACCCAATGACCTACTCCAAGA | SEQ ID NO. 25 |
| miR-584 | CTCAGTCCCAGGCAAACCATAA | SEQ ID NO. 26 |

The present invention provides a kit for detecting non-small cell lung cancer markers, that is, a kit for the prediction, diagnosis and/or evaluation of non-small cell lung cancer. The kit includes a tool to detect the markers mentioned above. Preferably, the tool includes a microRNA probe combination for detecting the non-small cell lung cancer markers; more preferably, the tool further includes polymerase and DNA. The non-small cell lung cancer diagnosis kit is prepared by collecting the screened microRNA primers with specific variations related to the non-small cell lung cancer or the matching probe sequences thereof into the PCR kit (RT-PCR or Real-time PCR).

The present invention also provides a biochip for detecting non-small cell lung cancer, that is, a biochip for predicting, diagnosing and/or evaluating non-small cell lung cancer, which includes a component for detecting the markers mentioned above. Preferably, the component comprises a microRNA probe combination for detecting the non-small cell lung cancer markers. The biochip for detecting microRNAs in serum or plasma specified for non-small cell lung cancer can be prepared by dotting the reverse compliment sequences of the selected microRNAs with varying specificity related to non-small cell lung cancer as probes on the chip.

More specifically, in each of the combinations, methods, kits or biochips that include the markers of 1 to 26 microRNAs described above, the evaluation of the aforesaid non-small cell lung cancer condition can be non-small cell carried out after the subjects have received drugs for treatment of non-small cell lung cancer, for the purpose of screening the activity of the drugs in the prevention and/or treatment of non-small cell lung cancer. Further, the evaluation of the aforesaid non-small cell lung cancer condition can be for the diagnosis and/or the differentiation of the disease of subjects. Still further, the evaluation of the aforesaid non-small cell lung cancer condition can be made to evaluate the efficacy of the treatment for the disease of the subjects, or non-small cell for prediction of the probability of non-small cell lung cancer occurrence or relapse.

The conventional techniques of biochemistry and molecular biology for clinical diagnosis are complex and not accurate enough. In the recent years, new techniques have been developed for disease diagnosis, including the gene chip and protein (anti-body) chip technique and the like. The mRNA level variations detected by the gene chip technique cannot reflect the actual variations of the protein level, because the bio-activity of the proteins is closely related with modifications such as glycosylation and phosphorylation after transcription. Also, for detecting many diseases, the gene chip technique cannot detect the marker molecules in the body fluid and blood. Meanwhile, the protein (antibody) chip technique and the proteomics technique are also limited. There are thousands of proteins and polypeptide segments in the human body, with an especially high concentration and distribution in the serum or plasma. Few proteins are definitely reported, and much fewer are quantified. It is a tremendous task to locate the proteins closely related to certain diseases amongst the numerous proteomes and understand their functions during the pathological process. Also, the development of anti-body chip technique is restrained by the lack of complete anti-body resources. On the contrary, by combining the unique characteristics of the serum or plasma microRNAs with conventional molecular biological detection techniques, it is for the first time possible to analyze rapidly and with high throughput the composition of non-small cell lung cancer serum or plasma microRNAs. Since the physiological variations in the condition of the organs and tissues cause variations in the composition of microRNAs in serum or plasma, microRNAs in serum or plasma can function as a fingerprint of disease for the early stage diagnosis of non-small cell lung cancer.

To summarize, the present invention provides the following advantages:
(1) The methods using screened microRNAs in serum or plasma as the markers of non-small cell lung cancer possess advantages including wide detection coverage, high sensitivity, low cost, convenient sample collection and preservation (serum or plasma can be preserved at −20° C.), among others. The method can be widely applied in general disease investigation and become an effective means for early diagnosis.
(2) Having serum or plasma microRNAs as novel disease markers can solve the problems of low specificity and sensitivity in signal marker detection method caused by unavoidable individual differences, will markedly improve the clinical detectability of diseases and achieve early diagnosis and treatment.
(3) The novel serum or plasma microRNA detection technique enable detection of a series of disease related markers, so that the influence from the individual differences of the patients (including age, gender, race, diet and environment conditions, and etc.) can be avoided, which is one of the major problems that single marker detection techniques cannot solve.

In summary, the present invention can be further applied in the early stage diagnosis of non-small cell lung cancer, and the novel markers of non-small cell lung cancer in serum or plasma do not only provide the foundation for understanding the mechanism of non-small cell lung cancer more fully at the molecular level, but also accelerate the advances in clinical diagnosis and treatment. It is quite apparent that, with the advantages of the serum or plasma microRNAs, the serum or plasma microRNAs diagnosis technique for severe diseases including cancer shall become part of general physical examination; as the genetic treatment related to microRNAs is being widely applied, these diseases shall be conquered.

PREFERRED EMBODIMENTS OF THE INVENTION

It should be understood that the embodiments described specifically herein are examples, which are not intended to limit the scope of the invention. The major features of the present invention can be applied in various embodiments without departing from the scope of the invention. It will be recognized by persons skilled in the art that the conventional experiments and many equivalents thereof may be applied in certain steps described above. Such equivalents are believed to be within the scope of the invention and covered by the appended claims.

Example 1: RT-PCR Experiments of microRNAs in Serum or Plasma

Using the RT-PCR assay, it has been shown that various microRNAs exist stably in serum or plasma of both human beings and other animals, and that their expression levels are considerably high. The specific steps are as follows:
(1) Collecting serum or plasma of mice, rats, normal subjects and patients with certain diseases.
(2) Preparing cDNA samples. This operation has two options: one is to directly conduct the reverse transcription reaction with 10 µl serum or plasma; the other is to firstly extract the total RNA from serum or plasma (usually, about 10 µg of RNA can be enriched by 10 µl of serum or plasma) with Trizol reagent (Invitrogen Co.), and then to obtain cDNA by the RNA reverse transcription reaction. The reaction system of reverse transcription comprises 4 µl of 5×AMV buffer, 2 µl, 10 mM of each dNTP mixture (Takara Co.), 0.5 µl of RNase Inhibitor (Takara Co.), 2 µl of AMV (Takara Co.) and 1.5 µl of gene specific reverse primer mixtures. The reaction steps successively include 15 minutes of incubation at 16° C., 1 hour of reaction at 42° C. and 5 minutes of incubation at 85° C.
(3) PCR and Electrophoresis observation. The cDNA is diluted in the ratio of 1/50. To 1 µl of diluted cDNA are added 0.3 µl of Taq polymerase (Takara Co.), 0.2 µl, 10 µM of forward primer, 0.2 µl, 10 µM of common reverse primer, 1.2 µl, 25 mM of $MgCl_2$, 1.6 µl, 2.5 mM of dNTP mixture (Takara Co.), 2 µl of 10×PCR buffer, 13.5 µl of $H_2O$, and PCR reaction is conducted in the 20 µl system. The PCR reaction is performed under the following conditions: one cycle at 95° C. for 5 mins followed by 40 cycles at 95° C. for 15 seconds and 60° C. for 1 minute. 10 µl of PCR product is subjected to 3% Agarose Gel Electrophoresis, which is observed under ultra violet lamp after EB staining.

Figure 2:
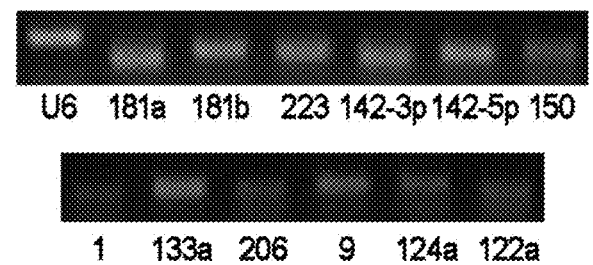
FIG. 2 shows the RT-PCR results of the microRNAs in the RNA extracted from the serum of a normal subject.

In FIG. 1 and FIG. 2, U6 is a snRNA with a molecular weight of 100bp, serving as an internal reference molecule in microRNAs experiments. The other 12 microRNAs are each miR-181a(181a), miR-181b(181b), miR-223(223), miR-142-3p(142-3p), miR-142-5p(142-5p), miR-150(150) from blood cells; miR-1(1), miR-133a(133a), miR-206(206) from cardiac muscles and skeletal muscles; miR-9(9), miR-124a(124a) from brain tissues; and miR-122a(122a) from liver.

The results are shown in FIG. 1, which shows the experimental results of RT-PCR directly conducted on the serum of normal subjects. In all, over 500 mature microRNAs of human beings were selected for conducting the RT-PCR reaction. Of these, the 12 microRNAs shown in FIG. 1 are, respectively, miR-181a, miR-181b, miR-223, miR-142-3p, miR-142-5p, miR-150 with blood cell specificity; miR-1, miR-133a, miR-206 from cardiac muscles and skeletal muscles; miR-9 and miR-124a from brain tissues; and miR-122a from liver. It can be seen from the results that all microRNAs from the four tissues mentioned above are detectable in blood. Meanwhile, not all of the total 500 mature microRNAs have high expression levels in the serum or plasma, and some are present only in extreme trace amounts and cannot be detected.

Figure 3:
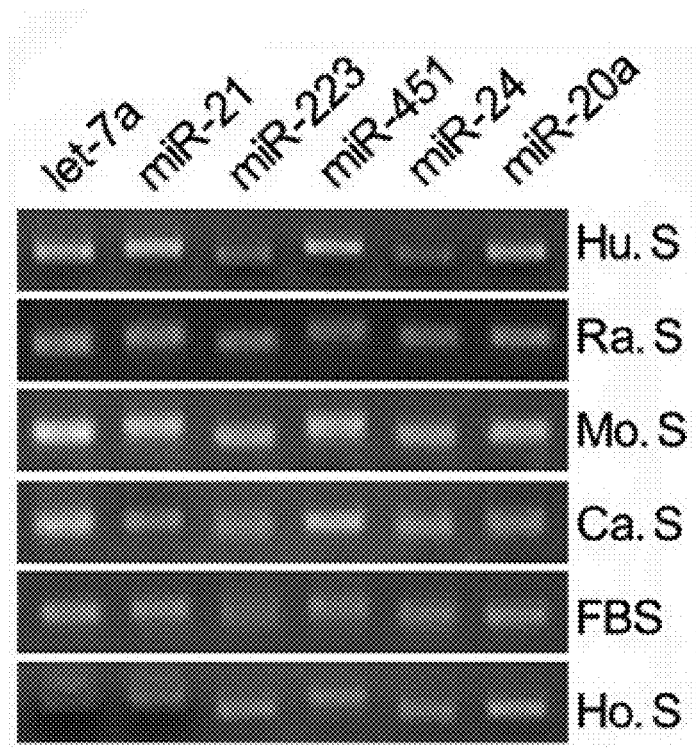
FIG. 3 shows the RT-PCR results of partial microRNAs directly detected in the serum of human, rat, mouse, calf, fetal bovine, and horse respectively.

To further verify that microRNAs exist stably in serum or plasma, RNA is extracted from the serum of normal subjects, and then over 500 mature microRNAs of human beings are selected for PCR experiment, the results of which are shown in FIG. 2. The results of FIG. 2 are quite consistent with those of FIG. 1, and the PCR products are simplex, which indicates that both assays can detect the expression and content of the microRNAs in human serum or plasma, and prove the stable existence of microRNAs in human serum or plasma from various tissue sources. In addition, the same method is used to detect the expression and abundance of over 500 microRNAs in the serum or plasma of mouse, rat, fetal bovine, calf and horse. It is also found that there is stable expression of microRNAs in serum or plasma from the various tissues sources of mouse, rat, fetal bovine, calf and horse (FIG. 3).

Example 2: Real-Time PCR Experiments of microRNAs in Serum or Plasma

Quantitative PCR experiments on serum or plasma microRNAs are conducted in order to study the specific variations of these microRNAs during the progression of non-small cell lung cancer. The principles and steps of the quantitative experiment are the same as that of RT-PCR, except that the fluorescent dye EVA GREEN is added during PCR. An ABI Prism 7300 fluorescent quantitative PCR system is used to conduct PCR reaction under the following conditions: one cycle at 95° C. for 5 mins followed by 40 cycles at 95° C. for 15 seconds and 60° C. for 1 minute. The data processing method is the ΔΔCT method, wherein CT is the number of cycles when the reaction reaches the threshold. The expression level of each microRNA relative to an internal standard reference can be expressed by the equation $2^{-\Delta CT}$, wherein $\Delta CT = CT_{sample} - CT_{internal\ reference}$. The reverse transcription reactions are directly conducted on serum or plasma samples of patients and normal subject, and the content of microRNAs in each sample of serum or plasma are compared by the quantitative PCR reactions.

The serum samples of patients with aplastic anemia, breast cancer, osteosarcoma, CNS (Central Nervous System) lymphoma and diabetes were selected, and over 500 mature microRNAs of human beings were used to conduct PCR reaction experiments. FIG. 4 shows the quantitative PCR results of selected microRNAs in the serum of patients and normal subjects, which include the above-mentioned miR-181a, miR-181b, miR-223, miR-142-3p, miR-142-5p, miR-150 with blood cell specificity; miR-1, miR-133a, miR-206 from cardiac muscles and skeletal muscles; miR-9, miR-124a from brain tissues; and miR-122a from liver. Compared with normal subjects, the microRNA content in serum of patients with aplastic anemia, breast cancer, osteosarcoma, CNS (Central Nervous System) lymphoma, diabetes is up or down-regulated, and the extent of variation in quantity of the microRNAs from the same tissue source differs in patients with different diseases, indicating that the variations of microRNAs in the serum or plasma of patients are specific to different diseases. Therefore, microRNAs can function as a novel class of markers for disease diagnosis.

Example 3: Biochip Utilizing Serum or Plasma microRNAs for the Diagnosis of Non-Small Cell Lung Cancer The operation steps of the biochip are as follows:

(1) Extracting the total RNA from serum or plasma, and measuring the mass of total RNA by formaldehyde denaturing gel electrophoresis.

(2) Separating microRNAs: microRNAs are separated with Ambion's microRNA Isolation Kit (Cat #. 1560) from 50-100 μg of total RNA.

(3) Conducting the fluorescent labeling on microRNA samples: the microRNA samples are labeled with fluorescent labeling using the T4RNA ligase labeling method, then precipitated using absolute ethanol, and then dried before hybridization to the biochip.

(4) Hybridizing and rinsing: RNAs are dissolved in 16 μl of hybridizing solution (15% formamide; 0.2% SDA; 3×SSC; 50×Denhardt's solution), hybridized overnight at 42° C. After hybridization, the RNAs are rinsed for 4 mins in a solution of 0.2% SDS, 2×SSC at about 42° C., and for 4 mins in the solution of 0.2% SDS, and then the biochips are spun dry for scanning.

(5) Scanning biochips: the chips are scanned with LuxScan 10K/A double channel laser scanner.

(6) Obtaining and analyzing data: the chip images are analyzed with LuxScan3.0 image analysis software so that the image signals are transferred into digital ones. Finally, the variation in gene expression is determined by SAM analysis.

The probes for the serum or plasma microRNAs with obvious variations in expression between different stages of non-small cell lung cancer and normal physiological status, which are double validated with the quantitative PCR technique and the biochip technique, are applied in the preparation of biochips using the same method as described above. Compared to conventional biochips, no distinct change is made in preparation and operation procedures; however, such biochips simplify the probe library, simplifying preparation and saving cost and time. Meanwhile, the pertinence and practicality of the biochips are improved. The biochips may be used to detect diseases in early stage and assist the diagnosis and treatment using only the serum or plasma, without the need to take any other tissues of patients.

Example 4: MicroRNA Kit for the Diagnosis and Prediction of Non-Small Cell Lung Cancer The preparation and use of the microRNA kit for the diagnosis of non-small cell lung cancer, prediction of complication occurrence and cancer relapse, evaluation of drug and treatment efficacy, and selection of the active elements from Chinese Traditional Medicine are based on the quantitative and semi-quantitative PCR, and the biochip method.

First, the microRNAs with more than one copy in normal serum or plasma are detected with the sequencing or the PCR technique. Then, the serum or plasma microRNAs with different expression levels and significant variations between non-small cell lung cancer samples in various stages of disease progression and subjects in normal physiological statuses are selected with the quantitative PCR technique and the biochip method. These may be used as indicators for the occurrence and progression of non-small cell lung cancer. Finally, 26 serum or plasma microRNAs are selected as diseases indicators, which form the most simplified probe library. The aforesaid kit comprises reagents including the serum or plasma microRNA primers, Taq polymerase and dNTP, and other reagents used in the amplification procedure.

In this example, all the detection samples are from patients diagnosed with non-small cell lung cancer and normal subjects in the same age and of the same gender as the patients (the control group).

First, the microRNAs with more than one copy in the normal serum or plasma are detected with the Solexa sequencing technique. By detecting the variations of the serum or plasma microRNAs, 91 microRNAs showing variations between the serum samples of non-small cell lung cancer patients and normal subjects (the control group) are selected, of which 60 microRNAs are up-regulated, and 31 microRNAs are down-regulated. For more detailed results, see Table 1.

TABLE 1

Sequencing results of expression variations of microRNAs in the serum samples of non-small cell lung cancer patients compared with the control group

| | Up-regulated microRNAs | | | | Down-regulated microRNAs | | |
|---|---|---|---|---|---|---|---|
| | | Number of microRNA copies | | | | Number of microRNA copies | |
| SN | microRNA | Normal samples | Non-small cell lung cancer samples | SN | microRNA | Normal samples | Non-small cell lung cancer samples |
| 1 | let-7b | 731 | 5443 | 1 | let-7f | 2009 | 61 |
| 2 | let-7c | 13 | 77 | 2 | let-7g | 2058 | 321 |
| 3 | miR-122 | 0 | 4471 | 3 | miR-100 | 26 | 0 |
| 4 | miR-125a-5p | 0 | 37 | 4 | miR-101 | 2510 | 14 |
| 5 | miR-125b | 0 | 37 | 5 | miR-106a | 158 | 0 |
| 6 | miR-128a | 0 | 296 | 6 | miR-106b | 1401 | 0 |
| 7 | miR-128b | 0 | 238 | 7 | miR-142-3p | 327 | 0 |
| 8 | miR-133a | 0 | 47 | 8 | miR-144 | 318 | 0 |
| 9 | miR-134 | 0 | 28 | 9 | miR-148a | 84 | 0 |
| 10 | miR-139-3p | 0 | 25 | 10 | miR-15a | 465 | 67 |
| 11 | miR-139-5p | 0 | 37 | 11 | miR-16 | 6806 | 900 |
| 12 | miR-145 | 0 | 23 | 12 | miR-17 | 557 | 54 |
| 13 | miR-146a | 109 | 2460 | 13 | miR-182 | 78 | 0 |
| 14 | miR-150 | 0 | 56 | 14 | miR-183 | 37 | 0 |
| 15 | miR-152 | 0 | 63 | 15 | miR-18a | 120 | 0 |
| 16 | miR-193a-5p | 0 | 58 | 16 | miR-194 | 79 | 12 |
| 17 | miR-197 | 0 | 75 | 17 | miR-19b | 484 | 14 |
| 18 | miR-199a-3p | 11 | 1485 | 18 | miR-20a | 1484 | 0 |
| 19 | miR-199a-5p | 0 | 32 | 19 | miR-20b | 99 | 0 |
| 20 | miR-205 | 0 | 23 | 20 | miR-29b | 25 | 0 |
| 21 | miR-22 | 168 | 928 | 21 | miR-340 | 109 | 12 |
| 22 | miR-221 | 0 | 5013 | 22 | miR-362-5p | 26 | 0 |
| 23 | miR-222 | 14 | 882 | 23 | miR-374a | 40 | 0 |
| 24 | miR-223 | 41 | 3446 | 24 | miR-424 | 23 | 0 |
| 25 | miR-23a | 13 | 2567 | 25 | miR-451 | 58299 | 8827 |
| 26 | miR-23b | 0 | 156 | 26 | miR-454 | 22 | 0 |
| 27 | miR-24 | 31 | 1689 | 27 | miR-7 | 477 | 0 |
| 28 | miR-25 | 739 | 8662 | 28 | miR-96 | 24 | 0 |
| 29 | miR-27a | 0 | 272 | 29 | miR-210 | 30 | 0 |
| 30 | miR-27b | 0 | 296 | 30 | miR-576-5p | 23 | 0 |
| 31 | miR-28-3p | 0 | 25 | 31 | miR-923 | 29 | 0 |
| 32 | miR-29a | 37 | 416 | | | | |
| 33 | miR-30a | 0 | 26 | | | | |
| 34 | miR-30d | 201 | 1575 | | | | |
| 35 | miR-320 | 526 | 12418 | | | | |
| 36 | miR-323-3p | 0 | 23 | | | | |
| 37 | miR-330-3p | 0 | 128 | | | | |
| 38 | miR-335 | 0 | 25 | | | | |
| 39 | miR-339-3p | 0 | 96 | | | | |
| 40 | miR-339-5p | 11 | 117 | | | | |
| 41 | miR-342-3p | 0 | 175 | | | | |
| 42 | miR-342-5p | 0 | 21 | | | | |
| 43 | miR-361-5p | 0 | 23 | | | | |
| 44 | miR-375 | 0 | 25 | | | | |
| 45 | miR-382 | 0 | 47 | | | | |
| 46 | miR-423-3p | 16 | 451 | | | | |
| 47 | miR-423-5p | 198 | 8708 | | | | |
| 48 | miR-432 | 0 | 37 | | | | |
| 49 | miR-433 | 0 | 26 | | | | |
| 50 | miR-486-3p | 0 | 116 | | | | |
| 51 | miR-495 | 0 | 70 | | | | |
| 52 | miR-543 | 0 | 44 | | | | |
| 53 | miR-574-3p | 0 | 42 | | | | |
| 54 | miR-584 | 0 | 163 | | | | |
| 55 | miR-598 | 0 | 65 | | | | |
| 56 | miR-744 | 0 | 174 | | | | |
| 57 | miR-92a | 339 | 4478 | | | | |
| 58 | miR-92b | 0 | 40 | | | | |
| 59 | miR-99a | 0 | 37 | | | | |
| 60 | miR-99b | 0 | 77 | | | | |

The 91 microRNAs with variations in the serum samples of non-small cell lung cancer compared with the normal subjects listed in Tab. 1 are further validated, and microRNAs with low expression (CT value>35) and variation less than 2-fold are excluded. Thus, 26 microRNAs are selected as the molecular markers for non-small cell lung cancer detection. For more detailed results, see Table 2.

TABLE 2 microRNAs with up-regulated expression in the serum samples of non-small cell lung cancer patients compared with normal subjects

| SN | microRNA | Average variation fold | P value (t test) |
|---|---|---|---|
| 1 | miR-7 | 2.412575969 | 0.005537233 |
| 2 | miR-20a | 2.261865218 | 0.00059758 |
| 3 | miR-23b | 6.458102663 | 0.002233957 |
| 4 | miR-24 | 2.186690805 | 0.000188172 |
| 5 | miR-25 | 2.68675329 | 0.002243975 |
| 6 | miR-27a | 4.028485241 | 0.000306088 |
| 7 | miR-29a | 2.853461454 | 0.00873306 |
| 8 | miR-30d | 16.6387221 | 0.008587796 |
| 9 | miR-99a | 4.77033723 | 0.002974451 |
| 10 | miR-125b | 3.140174768 | 6.4298E−05 |
| 11 | miR-144 | 2.013351794 | 2.9912E−05 |
| 12 | miR-145 | 2.005045799 | 0.000184252 |
| 13 | miR-146a | 2.591494056 | 1.56362E−05 |
| 14 | miR-152 | 5.004855185 | 0.005349185 |
| 15 | miR-182 | 3.184476141 | 0.00973501 |
| 16 | miR-199a-5p | 2.349659978 | 0.000124963 |
| 17 | miR-199a-3p | 2.325322005 | 7.70427E−05 |
| 18 | miR-221 | 2.664832913 | 4.96475E−08 |
| 19 | miR-222 | 2.345066984 | 6.43944E−08 |
| 20 | miR-223 | 9.78605432 | 0.000119161 |
| 21 | miR-320 | 3.154899532 | 1.41615E−08 |
| 22 | miR-375 | 8.449192106 | 0.000237439 |
| 23 | miR-382 | 3.45633594 | 0.000227961 |
| 24 | miR-423-5p | 11.33272015 | 0.007840799 |
| 25 | miR-432 | 3.51595148 | 7.09166E−05 |
| 26 | miR-584 | 3.163308445 | 7.99767E−05 |

Cluster analysis is conducted on the above-mentioned microRNAs to further demonstrate the existence of expression variations in the non-small cell lung cancer serum compared with the normal samples.

Figure 5A:
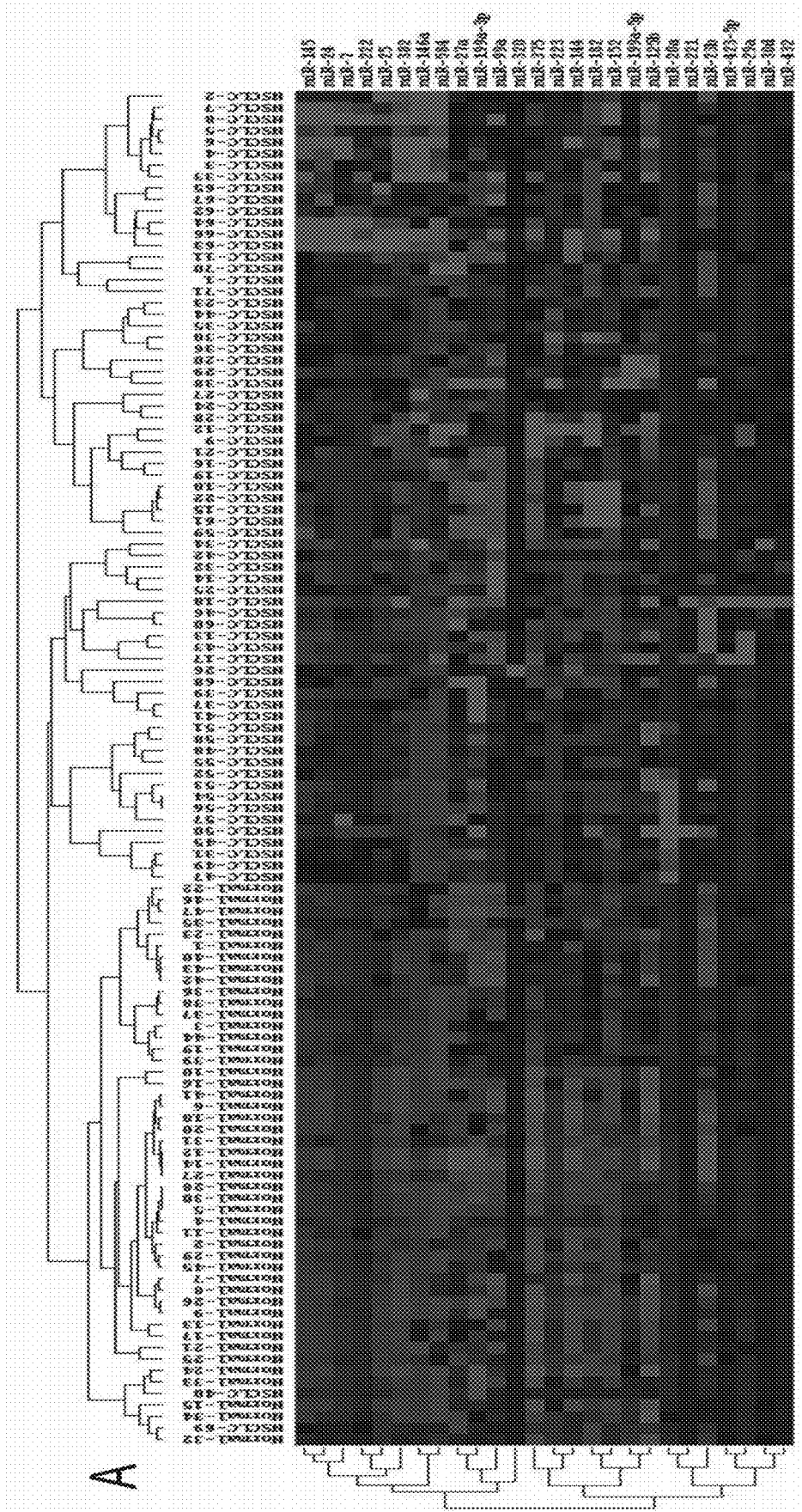
FIG. 5 (A-C) show the analysis results of the variable specificity of 26 specific serum or plasma microRNAs between normal subjects and non-small cell lung cancer patients.
Figure 5B:
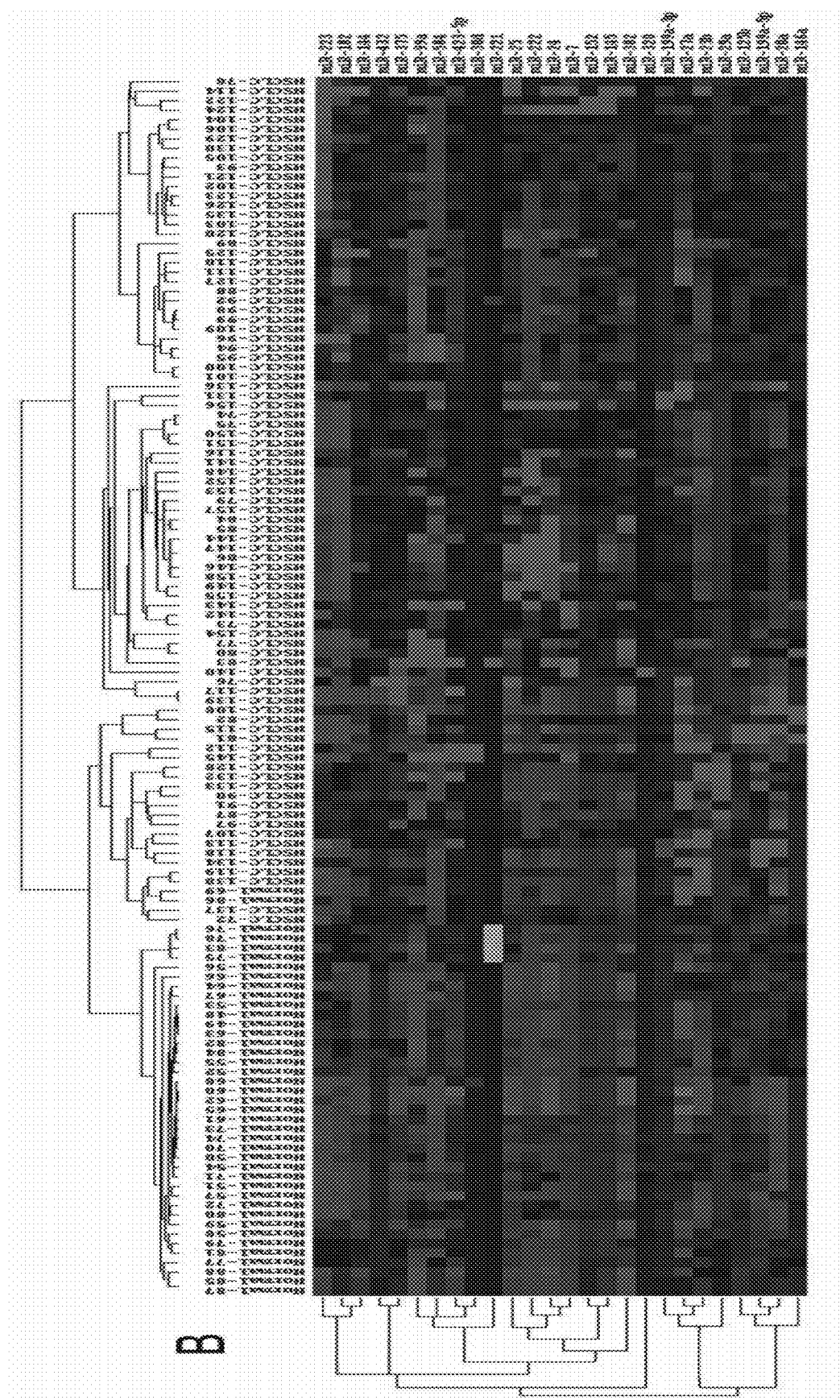
Figure 5C:
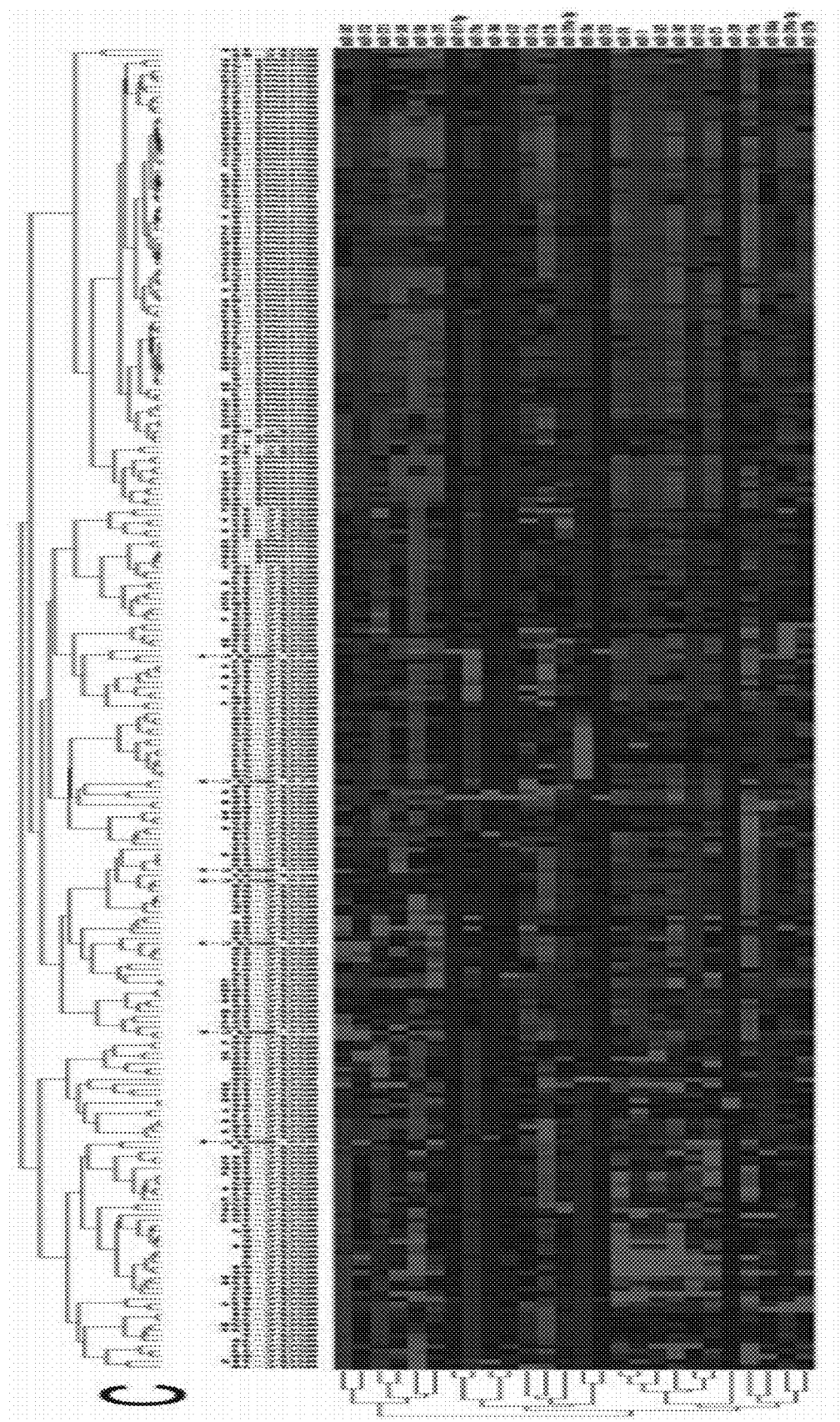

The data process procedure of cluster analysis is as follows: for the training group (FIG. 5-A, 71 patients and 47 controls), the validation group (FIG. 5-B, 87 patients and 41 controls) and all samples (FIG. 5-C, 158 patients and 88 controls), the absolute expression values of non-small cell lung cancer serum microRNAs are converted into ratios to that of the normal samples; FIG. 5 is drawn (using the software cluster 3.0) by normalizing and clustering the ratios, that is, having the 26 serum or plasma microRNAs as the analysis results of fingerprint specific variations of non-small cell lung cancer. As shown in FIG. 5, the cluster analysis shows that definite classification of the non-small cell lung cancer from the normal samples can be achieved based on the 26 microRNAs.

In FIG. 5-A, the tags at the right side represent the 26 microRNAs for detection; the tags above represent the individual samples for detection; "normal" represents the normal subjects (n=49), assembled at the left side of the figure; "nsclc" represents the non-small cell lung cancer patients (n=71), assembled at the right side of the figure. The figure demonstrates roughly that the detection on the expression levels of the 26 microRNAs can separate normal subjects from non-small cell lung cancer patients.

In FIG. 5-B, the tags at the right side represent the 26 microRNAs for detection, the tags above represent the individual samples for detection, "normal" represents the normal subjects (n=41), assembled at the left side of the figure; "nsclc" represents the non-small cell lung cancer patients (n=87), assembled at the right side of the figure. By enlarging the detection sample scale, the figure further demonstrates that the detection on the expression levels of the 26 microRNAs can separate normal subjects from non-small cell lung cancer patients.

FIG. 5-C is a combination of the samples in FIG. 5-A and FIG. 5-B, in which the analysis results of the fingerprint specific variations of the 26 microRNAs from 7 non-small cell lung cancer patients are demonstrated. The tags at the right side represent the 26 microRNAs for detection; the tags above represent the individual samples for detection; "normal" represents the normal subjects (88 samples), assembled at the right side of the figure; "nsclc" represents the non-small cell lung cancer patients (151 samples); and "pre-nsclc" represents the pre-non-small cell lung cancer patients (7 samples), that is, the blood samples extracted from non-small cell lung cancer patients before being diagnosed. The nsclc and pre-nsclc are both classified as non-small cell lung cancer patients, samples of whom are at the left side of the figure. The figure demonstrates again that the detection on the expression level of the 26 microRNAs can separate non-small cell lung cancer patients from normal subjects.

Risk scoring analysis is shown in FIG. 5, and detailed analysis results are listed in Tables 3 and 4, in which PPV stands for positive predictive value and NPV stands for the negative predictive value. In Table 3, in the first row the risk scoring marks of the assessing samples are listed, and in the second to sixth rows, the training group and the validation group under a certain risk scoring mark, the number of non-small cell lung cancer patients and of normal subjects are listed respectively; the statistical analysis is conducted with a statistical analysis software (SAS), and the risk scoring value is set as 4. If the risk scoring of the sample is ≥4, the sample is classified as that of a non-small cell lung cancer patient; and if the risk scoring of the sample is <4, the sample is classified as that of a normal subject.

The specific statistical analysis is performed as follows: besides each variable being controlled during the whole process, all the data shall be standardized into a zero-mean and a standard deviation before clustering. In order to minimize the influence of the missing values and to assist the layering of the clustering and risk scoring, the KNN (K-Nearest Neighbors, a technique based on missing data imputation) technique is applied to estimate the missing values in the $19^{th}$-$20^{th}$ interval. For example, if a missing value exists in the microRNAs of sample A, another K (number) microRNAs with the same expression level shall be detected in the same sample, and the samples with the most similar microRNA expression profile to sample A shall be detected. The missing value can be estimated by computing the weighted average of the K most similar microRNAs in sample A. The weighted average computation takes the expression similarity of each microRNA as its weighted value. The K herein is set as 9, which means 9 neighboring microRNAs are included in the computation. Besides, the computation results obtained from the KNN technique have little effect on the current research conclusions, because the invocation rate of all markers is higher than 97.6%, and there is no sample missing two or more than two markers.

The layering of the clustering with the complete associated mode in cluster 3.0 is applied in the statistics. To conduct risk scoring, 95% of the upper limit of the value reference interval of each microRNA in the control group is set as t, being the threshold value controlling the expression level encoding of microRNAs from each sample. The risk scoring of each microRNA is denoted as S, which can be expressed with the equation:

$$s_{ij} = \begin{cases} 0 & \text{if } r_{ij} < t_j \\ 1 & \text{otherwise} \end{cases}$$

in which i stands for the $i^{th}$ sample, $\hat{j}$ stands for the $j^{th}$ microRNA. Considering that the assessment of the weighted values of the microRNA in non-small cell lung cancer are different, a risk scoring function is formed for each patient based on the linear combination of the microRNA expression levels. In accordance with the related materials of the K microRNAs, the risk scoring function of sample i is:

$$rsf_i = \sum_{j=1}^{k} \text{sign}_j \cdot W_j \cdot s_{ij}$$

Wherein, $s_{ij}$ is the risk scoring of microRNA $\hat{j}$ from sample i, and $W_j$ is the weighted value of microRNA $\hat{j}$ in risk scoring. To determine sign and $W_j$, the fitting application with the Logistic Regression Model with 10 single variables is conducted on the subjects with risk scoring values. The regression coefficient of each risk scoring is used as the weighted value of each microRNA in the risk scoring function, and the sign in the regression coefficient determines the sign in the risk scoring function. The diagnosis effect of the sample group is evaluated with the frequency table and the ROC curve.

TABLE 3

Risk scoring of patients and controls (normal subjects)

| | Risk scoring | 0 | 1 | 2 | 3 | 4 | 5 | 6 | 7 | 8 | 9 | 10 | 11 |
|---|---|---|---|---|---|---|---|---|---|---|---|---|---|
| Training group (FIG. 5-A) | NSCLC | 0 | 0 | 3* | 1 | 3 | 3 | 6 | 3 | 8 | 2 | 7 | 7 |
| | Normal | 18 | 12 | 10 | 3 | 3 | 1 | 0 | 0 | 0 | 0 | 0 | 0 |
| Validation group (FIG. 5-B) | NSCLC | 0 | 0 | 1 | 2 | 3 | 5 | 8 | 10 | 6 | 12 | 7 | 5 |
| | Normal | 17 | 8 | 10 | 6 | 0 | 0 | 0 | 0 | 0 | 0 | 0 | 0 |
| Combination (FIG. 5-C) | NSCLC | 0 | 0 | 4 | 3 | 6 | 8 | 14 | 13 | 14 | 14 | 14 | 12 |
| | Normal | 35 | 20 | 20 | 9 | 3 | 1 | 0 | 0 | 0 | 0 | 0 | 0 |

| | Risk scoring | 12 | 13 | 14 | 15 | 16 | 17 | 18 | 19 | Total number of subjects | PPV | NPV |
|---|---|---|---|---|---|---|---|---|---|---|---|---|

TABLE 3-continued

Risk scoring of patients and controls (normal subjects)

| Training group (FIG. 5-A) | NSCLC | 3 | 5 | 6 | 6 | 3 | 0 | 3 | 2 | 71 | 0.94 | |
| --- | --- | --- | --- | --- | --- | --- | --- | --- | --- | --- | --- | --- |
| | Normal | 0 | 0 | 0 | 0 | 0 | 0 | 0 | 0 | 47 | | 0.91 |
| Validation group (FIG. 5-B) | NSCLC | 2 | 8 | 7 | 5 | 2 | 2 | 0 | 2 | 87 | 0.97 | |
| | Normal | 0 | 0 | 0 | 0 | 0 | 0 | 0 | 0 | 41 | | 1 |
| Combination (FIG. 5-C) | NSCLC | 5 | 13 | 13 | 11 | 5 | 2 | 3 | 2 | 158 | 0.96 | |
| | Normal | 0 | 0 | 0 | 0 | 0 | 0 | 0 | 0 | 88 | | 0.95 |

TABLE 4

Risk scoring of pre-cancer patients

| | Sample | | | | | | |
| --- | --- | --- | --- | --- | --- | --- | --- |
| | B-1 | B-2 | B-3 | B-4 | B-5 | B-6 | B-7 |
| Age (years) | 76 | 59 | 42 | 70 | 53 | 52 | 71 |
| Gender | F | F | M | M | M | M | M |
| Smoking history | No | No | No | Yes | Yes | Yes | Yes |
| Time in advance (months)* | 33.37 | 26.47 | 8.23 | 2.03 | 9.4 | 23.17 | 0.7 |
| Phase classification | IV | III | | | II | I | |
| Prognosis | Dead | Dead | Dead | Dead | Alive | Alive | Dead |
| Direct scoring | 10 | 4 | 3 | 2 | 2 | 1 | 4 |

In Table 4, * represents that the diagnosis time is the time of blood extracting, and ** represents that the time of death is the diagnosis time.

It can be seen from Table 4 that, in the cases of pre-cancer patients, this detection method can distinguish the patients with unfavorable prognosis from those with favorable prognosis and the normal subjects.

Therefore, Tables 3 and 4 show that variations happen to any of the 26 detected microRNAs. The threshold value is set as follows: compared with the normal samples, if four or more than four microRNAs with significant expression variations are detected from the samples, a non-small cell lung cancer patient can be diagnosed. The results show that each microRNA can be used as a marker for non-small cell lung cancer, that is, any one or any combination of the 26 microRNAs can be used as non-small cell lung cancer markers.

Figure 6:
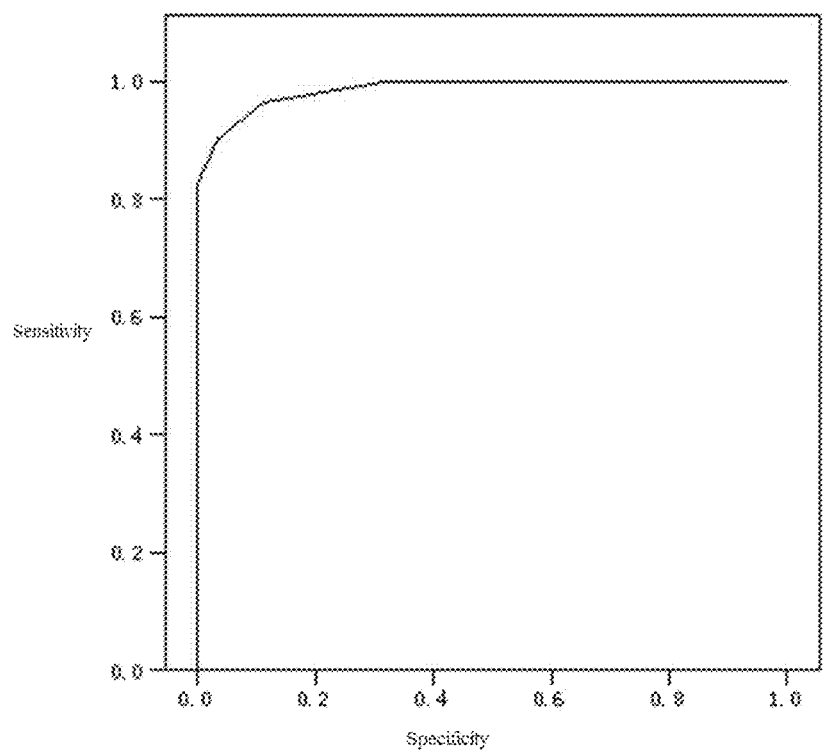
FIG. 6 shows a schematic illustration of the sensitivity and specificity of microRNAs in the detection of non-small cell lung cancer.

FIG. 6 is a schematic illustration of the sensitivity and specificity of non-small cell lung cancer detection with microRNAs. Given that the total area (the total number of detection samples) is 1, the area under curve (i.e. reliability) reaches 0.986.

Figure 7:
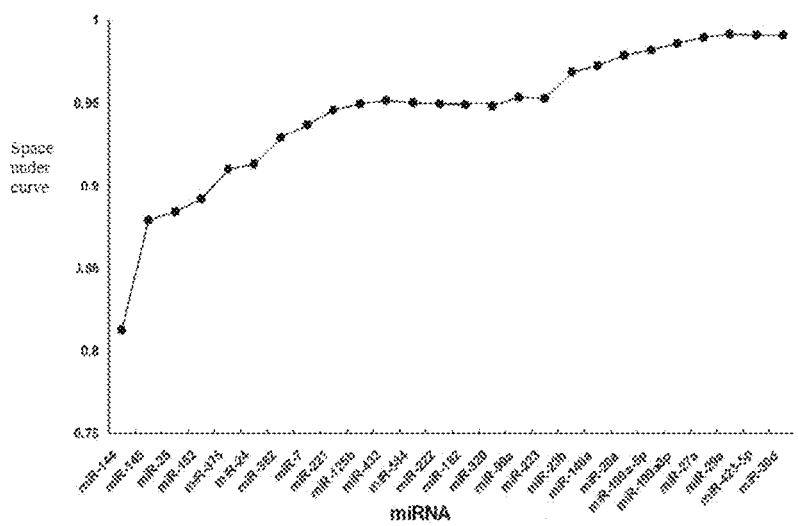
FIG. 7 shows a graph of the accuracy of the 26 microRNAs in the detection of non-small cell lung cancer.

FIG. 7 shows the reliability of non-small cell lung cancer detection with the 26 microRNAs, in which the horizontal axis stands for the types of detected microRNAs, and the vertical axis which is denoted as the area under curve, stands for the reliability of non-small cell lung cancer detection with the 26 microRNAs (given that the total area (the total number of detection samples) is 1). FIG. 7 shows that the reliability of the detection method in the present invention with the above-mentioned microRNAs as the detection marker is higher than 0.98.

In summary, the importance of the kit in the present invention lays in that the prediction of the possibility of non-small cell lung cancer occurrence or the diagnosis of the pathological stages of non-small cell lung cancer can be achieved with the most simplified probe library that detects the variation trend of microRNAs with only serum or plasma but without any other tissue samples. Therefore, putting the kit into practice can promote the early detection of non-small cell lung cancer and assist the diagnosis and treatment of the disease.

What is claimed is:

1. A set of microRNA probes for detecting non-small cell lung cancer markers in a serum or plasma sample, wherein said set of microRNA probes consists of microRNA probes that specifically bind to the following markers: miRNA-25, miRNA-145, miRNA-221, and miRNA-125a-5p, wherein the microRNA probes are detectably labeled.

2. The set of microRNA probes of claim 1, wherein each of the said microRNA probes is labeled with an isotope or a fluorescent.

3. The set of microRNA probes of claim 1, wherein said set of microRNA probes comprises an oligomer with the nucleobase sequence of SEQ ID NO: 5, an oligomer with the nucleobase sequence of SEQ ID NO: 12, and an oligomer with the nucleobase sequence of SEQ ID NO: 18.

4. The set of microRNA probes of claim 1, wherein each of the said microRNA probes is fixed on a substrate to form a biochip.

5. A kit for detecting non-small cell lung cancer in a serum or plasma sample comprising:
a container in which a set of microRNA probes is contained;
primers configured to amplify microRNA markers in the serum or plasma sample, wherein the microRNA markers consist of miRNA-25, miRNA-145, miRNA-221, and miRNA-125a-5p;
reagents configured to extract or enrich the microRNA markers in the serum or plasma sample;
a polymerase, a deoxynucleotide or a deoxyribonucleotide; and
a specification;
wherein, said set of microRNA probes consists of microRNA probes that specifically bind to the following microRNA markers: miRNA-25, miRNA-145, miRNA-221, and miRNA-125a-5p, and wherein the microRNA probes are detectably labeled.

6. The kit of claim 5, wherein the set of microRNA probes comprises probe-miRNA-25 (SEQ ID NO: 5), probe-miRNA-145 (SEQ ID NO: 12), and probe-miRNA-221 (SEQ ID NO: 18).

7. The kit of claim 5, wherein said polymerase is Taq polymerase.

8. The kit of claim 5, wherein said set of microRNA probes are fixed on a substrate to form a biochip.

9. A method for detection of a tumor wherein the tumor is non-small cell lung cancer and the method comprises:
(a) providing a serum or plasma sample of a subject;
(b) detecting presence and amount of microRNA markers consisting of miRNA-25, miRNA-145, miRNA-221, and miRNA-125a-5p in the serum or plasma sample by detecting an amount of binding of a set of microRNA probes according to claim 1 to said microRNA markers so as to obtain a measured value of the amount of binding; and
(c) comparing the measured value with a standard value, wherein if the measured value is significantly higher than the standard value, the subject is more susceptible to or suffers from non-small cell lung cancer.

10. The method of claim 9, wherein the microRNA probes are labeled with an isotope.

11. The method of claim 9, wherein the microRNA probes are labeled with a fluorescent.

12. The method of claim 9, wherein the subject is human.

13. The method of claim 9, wherein the sample is a serum sample.

\* \* \* \* \*

SEQUENCE LISTING

<160> NUMBER OF SEQ ID NOS: 26

<210> SEQ ID NO 1
<211> LENGTH: 22
<212> TYPE: DNA
<213> ORGANISM: artificial sequence
<220> FEATURE:
<223> OTHER INFORMATION: oligonucleotide

<400> SEQUENCE: 1
caacaaaatc actagtcttc ca                                        22

<210> SEQ ID NO 2
<211> LENGTH: 23
<212> TYPE: DNA
<213> ORGANISM: artificial sequence
<220> FEATURE:
<223> OTHER INFORMATION: oligonucleotide

<400> SEQUENCE: 2
ctacctgcac tataagcact tta                                       23

-continued

```
<210> SEQ ID NO 3
<211> LENGTH: 21
<212> TYPE: DNA
<213> ORGANISM: artificial sequence
<220> FEATURE:
<223> OTHER INFORMATION: oligonucleotide

<400> SEQUENCE: 3
ggtaatccct ggcaatgtga t                                                 21

<210> SEQ ID NO 4
<211> LENGTH: 22
<212> TYPE: DNA
<213> ORGANISM: artificial sequence
<220> FEATURE:
<223> OTHER INFORMATION: oligonucleotide

<400> SEQUENCE: 4
ctgttcctgc tgaactgagc ca                                                22

<210> SEQ ID NO 5
<211> LENGTH: 22
<212> TYPE: DNA
<213> ORGANISM: artificial sequence
<220> FEATURE:
<223> OTHER INFORMATION: oligonucleotide

<400> SEQUENCE: 5
tcagaccgag acaagtgcaa tg                                                22

<210> SEQ ID NO 6
<211> LENGTH: 21
<212> TYPE: DNA
<213> ORGANISM: artificial sequence
<220> FEATURE:
<223> OTHER INFORMATION: oligonucleotide

<400> SEQUENCE: 6
gcggaactta gccactgtga a                                                 21

<210> SEQ ID NO 7
<211> LENGTH: 21
<212> TYPE: DNA
<213> ORGANISM: artificial sequence
<220> FEATURE:
<223> OTHER INFORMATION: oligonucleotide

<400> SEQUENCE: 7
aaccgatttc agatggtgct a                                                 21

<210> SEQ ID NO 8
<211> LENGTH: 22
<212> TYPE: DNA
<213> ORGANISM: artificial sequence
<220> FEATURE:
<223> OTHER INFORMATION: oligonucleotide

<400> SEQUENCE: 8
cttccagtcg gggatgttta ca                                                22

<210> SEQ ID NO 9
<211> LENGTH: 22
<212> TYPE: DNA
<213> ORGANISM: artificial sequence
<220> FEATURE:
```

<223> OTHER INFORMATION: oligonucleotide

<400> SEQUENCE: 9
cacaagatcg gatctacggg tt					22

<210> SEQ ID NO 10
<211> LENGTH: 22
<212> TYPE: DNA
<213> ORGANISM: artificial sequence
<220> FEATURE:
<223> OTHER INFORMATION: oligonucleotide

<400> SEQUENCE: 10
tcacaagtta gggtctcagg ga					22

<210> SEQ ID NO 11
<211> LENGTH: 22
<212> TYPE: DNA
<213> ORGANISM: artificial sequence
<220> FEATURE:
<223> OTHER INFORMATION: oligonucleotide

<400> SEQUENCE: 11
ctagtacatc atctatactg ta					22

<210> SEQ ID NO 12
<211> LENGTH: 24
<212> TYPE: DNA
<213> ORGANISM: artificial sequence
<220> FEATURE:
<223> OTHER INFORMATION: oligonucleotide

<400> SEQUENCE: 12
aagggattcc tgggaaaact ggac					24

<210> SEQ ID NO 13
<211> LENGTH: 22
<212> TYPE: DNA
<213> ORGANISM: artificial sequence
<220> FEATURE:
<223> OTHER INFORMATION: oligonucleotide

<400> SEQUENCE: 13
aacccatgga attcagttct ca					22

<210> SEQ ID NO 14
<211> LENGTH: 22
<212> TYPE: DNA
<213> ORGANISM: artificial sequence
<220> FEATURE:
<223> OTHER INFORMATION: oligonucleotide

<400> SEQUENCE: 14
cccaagttct gtcatgcact ga					22

<210> SEQ ID NO 15
<211> LENGTH: 22
<212> TYPE: DNA
<213> ORGANISM: artificial sequence
<220> FEATURE:
<223> OTHER INFORMATION: oligonucleotide

<400> SEQUENCE: 15
tgtgagttct accattgcca aa					22

```
<210> SEQ ID NO 16
<211> LENGTH: 23
<212> TYPE: DNA
<213> ORGANISM: artificial sequence
<220> FEATURE:
<223> OTHER INFORMATION: oligonucleotide

<400> SEQUENCE: 16
gaacaggtag tctgaacact ggg                                              23

<210> SEQ ID NO 17
<211> LENGTH: 22
<212> TYPE: DNA
<213> ORGANISM: artificial sequence
<220> FEATURE:
<223> OTHER INFORMATION: oligonucleotide

<400> SEQUENCE: 17
taaccaatgt gctctgatga ca                                               22

<210> SEQ ID NO 18
<211> LENGTH: 23
<212> TYPE: DNA
<213> ORGANISM: artificial sequence
<220> FEATURE:
<223> OTHER INFORMATION: oligonucleotide

<400> SEQUENCE: 18
gaaacccagc agacaatgta gct                                              23

<210> SEQ ID NO 19
<211> LENGTH: 24
<212> TYPE: DNA
<213> ORGANISM: artificial sequence
<220> FEATURE:
<223> OTHER INFORMATION: oligonucleotide

<400> SEQUENCE: 19
gagacccagt agccagatgt agct                                             24

<210> SEQ ID NO 20
<211> LENGTH: 21
<212> TYPE: DNA
<213> ORGANISM: artificial sequence
<220> FEATURE:
<223> OTHER INFORMATION: oligonucleotide

<400> SEQUENCE: 20
ggggtatttg acaaactgac a                                                21

<210> SEQ ID NO 21
<211> LENGTH: 23
<212> TYPE: DNA
<213> ORGANISM: artificial sequence
<220> FEATURE:
<223> OTHER INFORMATION: oligonucleotide

<400> SEQUENCE: 21
ttcgccctct caacccagct ttt                                              23

<210> SEQ ID NO 22
<211> LENGTH: 22
<212> TYPE: DNA
<213> ORGANISM: artificial sequence
<220> FEATURE:
<223> OTHER INFORMATION: oligonucleotide
```

```
<400> SEQUENCE: 22
tcacgcgagc cgaacgaaca aa                                              22

<210> SEQ ID NO 23
<211> LENGTH: 22
<212> TYPE: DNA
<213> ORGANISM: artificial sequence
<220> FEATURE:
<223> OTHER INFORMATION: oligonucleotide

<400> SEQUENCE: 23
cgaatccacc acgaacaact tc                                              22

<210> SEQ ID NO 24
<211> LENGTH: 22
<212> TYPE: DNA
<213> ORGANISM: artificial sequence
<220> FEATURE:
<223> OTHER INFORMATION: oligonucleotide

<400> SEQUENCE: 24 ctgagggcc tcagaccgag ct                                               22

<210> SEQ ID NO 25
<211> LENGTH: 23
<212> TYPE: DNA
<213> ORGANISM: artificial sequence
<220> FEATURE:
<223> OTHER INFORMATION: oligonucleotide

<400> SEQUENCE: 25
ccacccaatg acctactcca aga                                             23

<210> SEQ ID NO 26
<211> LENGTH: 22
<212> TYPE: DNA
<213> ORGANISM: artificial sequence
<220> FEATURE:
<223> OTHER INFORMATION: oligonucleotide

<400> SEQUENCE: 26
ctcagtccca ggcaaaccat aa                                              22
```